United States Patent [19]

Dietz et al.

[11] Patent Number: 4,532,013
[45] Date of Patent: Jul. 30, 1985

[54] METHOD FOR MONITORING OPERATION OF A CURRENT-LIMITING TYPE GAS SENSOR

[75] Inventors: Hermann Dietz, Gerlingen; Ferdinand Grob, Besigheim; Klaus Müller, Tamm; Harald Reber, Gerlingen, all of Fed. Rep. of Germany

[73] Assignee: Robert Bosch GmbH, Stuttgart, Fed. Rep. of Germany

[21] Appl. No.: 357,622

[22] Filed: Mar. 12, 1982

[30] Foreign Application Priority Data

Apr. 16, 1981 [DE] Fed. Rep. of Germany ....... 3115404

[51] Int. Cl.³ ............................................. G01N 27/46
[52] U.S. Cl. .................................... 204/1 T; 204/401; 204/402; 204/425; 204/429
[58] Field of Search ........................ 204/424–429, 204/401, 1 T, 15, 402

[56] References Cited

U.S. PATENT DOCUMENTS

| | | | |
|---|---|---|---|
| 2,955,206 | 10/1960 | Spergel et al. | 250/359.1 |
| 3,429,784 | 2/1969 | Molloy | 204/415 |
| 3,691,023 | 9/1972 | Ruka et al. | 204/425 |
| 3,740,533 | 6/1973 | Van Zeggelaar | 364/176 |
| 4,231,733 | 11/1980 | Hickam et al. | 204/427 |
| 4,306,957 | 12/1981 | Ishitani et al. | 204/426 |
| 4,356,065 | 10/1982 | Dietz | 204/429 |
| 4,384,925 | 5/1983 | Stetter et al. | 204/401 |

FOREIGN PATENT DOCUMENTS

| | | |
|---|---|---|
| 2929532 | 2/1981 | Fed. Rep. of Germany . |
| 1209402 | 10/1970 | United Kingdom . |
| 2054204 | 2/1981 | United Kingdom . |

Primary Examiner—T. Tung
Attorney, Agent, or Firm—Frishauf, Holtz, Goodman & Woodward

[57] ABSTRACT

To permit calibrating and testing a current-limiting sensor in situ, the sensor is exposed, from time to time, to ambient air forming a standard gas, and the output thereof compared with a standard, for example by connecting a resistor (4) of standard value in circuit therewith or for recalling from a memory (23) in a microcomputer (22) standard conditions; upon determination of a deviation between output from the sensor (2) when exposed to the standard gas—typically air—and the theoretical value as stored, the theoretical or reference value is reset if the deviation is within a predetermined limit or, otherwise, an alarm output is provided. The tolerance limits can be set in such a way that a first alarm output is provided in a narrow tolerance, thus indicating drift of the sensor toward eventual malfunction, and permitting utilization of the sensor for long lifetime, while providing advance warning of imminent failure. Change of applied voltage to the sensor and test for current therethrough can then derive an actual operating curve which can be compared with stored test curves in the memory from which, upon extrapolation, a tendency to failure can be predicted and recognized.

11 Claims, 6 Drawing Figures

METHOD FOR MONITORING OPERATION OF A CURRENT-LIMITING TYPE GAS SENSOR

The present invention relates to gas sensors and more particularly to gas sensors of the current-limiting type in which a solid electrolyte body has electrodes applied thereto, and the limiting current, upon application of a voltage across the electrodes, is determined. Such sensors are particularly adapted to determine the oxygen content in the combustion exhaust gases, for example exhaust gases in smokestacks and particularly exhaust gases emanating from internal combustion engines, for example automotive-type gasoline fuel internal combustion engines. The present invention is specifically concerned with monitoring the operation of such sensors and calibrating the outputs derived therefrom.

BACKGROUND

Current-limiting sensors are known, and reference is made to, for example, U.S. application Ser. No. 213,049, filed Dec. 4, 1980, Dietz, now U.S. Pat. No. 4,356,065 assigned to the asignee of the present application, which describes a sensor structure providing an analog output signal representative of oxygen contentration of a gas to which the sensor is exposed. Calibration of such sensors is difficult. It is possible to remove the sensor from the apparatus with which it is associated, for example an exhaust system of an internal combustion (IC) engine and introduce the sensor into a measuring or test apparatus, in which a test program is run which checks if typical values appropriate for the sensor are being maintained. It was not possible to test the sensor when it is in actual operation or association with the engine. If, in due course and due to aging, for example, the output signals from the sensor vary with respect to given gas compositions derived from the engine, exchange of the sensor is required or the associated electrical evaluation circuitry must be recalibrated. Small changes in output signals with a given test gas can usually not be recognized when the sensor is installed in a motor vehicle. Even if the sensor were entirely inoperative, or so severely damaged as not to provide reasonable or expected output signals, a substantial period of time may elapse before it is recognized that the sensor is damaged and should be replaced. In the meanwhile, erroneous engine operation may be commanded by output signals derived from the sensor.

THE INVENTION

It is an object to provide a test and calibration method and apparatus to determine if operation of a sensor is within given limits and, further, to calibrate the output signals derived therefrom if the sensor is still sufficiently operative to permit recalibration of the associated equipment, so that the sensor operation, effectively, can be controlled in its actual environment, that is, as installed in a combustion exhaust system.

Briefly, the sensor is subjected, intermittently, to a standard gas of known composition. A typical standard gas is ambient air. The sensor output with the standard gas is then determined. A standard reference value is provided, representative of sensor output when subjected to the standard gas. The measured output from the sensor, with the standard gas applied, is then compared with the standard reference value to obtain a deviation signal if the measured output and the standard reference value do not agree. The magnitude of the deviation signal is determined and utilized to reset the evaluation circuitry to null the deviation. If the deviation should exceed a predetermined limit, however, an alarm signal is given. The correction can be carried out in an adaptive mode by updating or resetting the magnitude of the standard reference value to conform to the measured output if the deviation signal is greater than zero, but below a predetermined level. Exceeding the predetermined level is an indication that the sensor can no longer function in the evaluation system with which it is being used.

The method and apparatus of the present invention have the advantage that the sensor can be tested while it is installed in an existing exhaust system; it can be monitored together with the associated measuring and evaluation and/or control circuitry, to provide for recalibration as response characteristics of the sensor change, if such recalibration is possible. Alternatively, a malfunction alarm can be obtained.

Recalibrating the evaluation or associated circuitry permits long use of existing sensors since those sensors which fall within the tolerance range of operation can continue to be used. Yet, erroneous outputs from those sensors are avoided since the associated circuitry has been recalibrated to compensate for changes in output of the sensor.

When installed in automotive vehicle, ambient air is particularly suitable as a reference gas. Ambient air can be introduced to a sensor in the exhaust system of a vehicle, for example, by carrying out the test some time after the engine has been stopped. After elapse of a suitable interval, ambient air will penetrate into the exhaust manifold, or exhaust gas system and will form a suitable reference value at that time. Alternatively, a bypass duct can be used which is selectively connectable to the combustion exhaust gas or to ambient air.

In accordance with a particularly advantageous feature of the invention, a characteristic curve is derived from a commanded current-limiting value, which, then, permits generation of characteristic curves which may be non-linear. If the deviation of actual sensor current from commanded, or nominal sensor current exceeds a predetermined limit, the sensor can be disconnected in its entirety since the conclusion can be reached that the entire sensor is defective.

Ambient air is particularly suitable as a standard reference gas. In accordance with a desirable feature of the invention, the sensor current, or sensor characteristics determined upon the last test with a reference gas, typically ambient air, is stored and the stored value is then utilized to correct the characteristic curve of the sensor output signals. This is a particularly simple embodiment of the invention. More than one sensor current value can be stored and then an extrapolation step can be carried out over and beyond the last sensor current value. This permits detection of errors of the sensor at an early time, so that the sensor can be exchanged, if necessary, before complete failure thereof.

Current-limiting sensors are supplied with current from a source of predetermined voltage value. In accordance with a feature of the invention, the supply voltage of the source is varied about a predetermined nominal value, and the charge in current, upon change in voltage is measured. Determination of the relative change in current/change in voltage gives information to determine if the sensor characteristics change excessively, or within predetermined limits. To avoid erroneous outputs, voltage changes are preferably commanded at a frequency of less than one Hz. Preferably, the command current value is determined shortly before the sensing apparatus is connected, for example shortly before starting of an IC engine, since the sensor has been subjected to ambient air after the engine has been stopped for an appreciable period of time. Test steps can also be carried out each time when a predetermined interval after last stopping the engine has elapsed.

Recalibration of the sensor accessory apparatus, including its evaluation circuitry, is simply carried out by using an adjustable dc voltage source, which is controllable by control circuitry to derive a reference sensor current value. The dc voltage source is preferably formed as a resistor, the value of which can change, for example by a servo motor moving a slider of a potentiometer. Other control systems may be used. An adjustable resistor, for example when motor controlled, then will have the function of a sensor command current memory, by merely stopping the motor at the selected resistance position. A control circuit is easily constructed by utilizing fixed resistors in combination with a variable resistor, the fixed resistance values of the resistors being changed upon change of sensor current. The control circuitry can then be used both for testing, or monitoring operation of the sensor as well as for calibrating the evaluation or accessory circuitry. Preferably, a motor-operated potentiometer is formed with end switches which, when contacted by the slider at the end of travel of the motor change a fixed resistance value to a different level or, when a limit has been reached disconnecting the control system, and providing a corresponding output indication. Large deviations of sensor current can thus be recognized.

In accordance with a feature of the invention, monitoring and calibrating of current-limiting sensors can also be carried out by utilizing a computer apparatus, such as a micro computer which can be employed for control functions as well as for storage of sensor values. Micro computers, with built-in memories, have the additional advantage that various characteristic curves can be addressed, stored, for example, in read-only memories (ROMs). By using, for example, programable ROMs (PROMs), various types of sensors can be used with such a system. The computer apparatus can also control the dc voltage of the dc voltage source in order to test the change in current limiting values of the sensor. Micro computers readily permit extrapolation if at least two earlier sensed values of limiting current have been stored in the memory thereof. A tendency to failure of the sensor thus can be recognized early and before the sensor has actually failed.

When predetermined current-limiting values are exceeded in either direction, or if the change between two sequential tests exceeds a predetermined value, error alarms can be triggered by computer apparatus; alternatively, the computer apparatus may retain in its memory an emergency program which provides for simulated sensor output to control associated apparatus, such as an IC engine, in accordance with predetermined data based on average operating conditions so that the engine will still function although not necessarily at its best, or most efficient or proper characteristic. Total failure of the associated apparatus has been avoided, however. Damage to the sensor thus can be sensed in good time before the overall system with which the sensor is used must be disabled.

A single-chip micro computer is particularly suitable as computation apparatus.

The present invention is adapted for use with sensors in all types of combustion processes, such as furnaces, heating installations, or in vehicles using internal combustion engines. In all such installations, ambient air can be used as a standard or comparision gas for testing of the sensors.

DRAWINGS

The invention will be described in connection with a sensor used to determine the oxygen concentration in the exhaust gases from an internal combustion (IC) engine. The air-fuel composition of the gas supplied to the engine can be controlled by determining the composition of the exhaust gases; similarly, appropriate or optimum adjustment of fuel and air to any combustion system, such as a furnace, heater or burner arrangement can be determined by use of a current-limiting sensor to control the air-fuel ratio of the supply to the burner or furnace.

Figure 1:
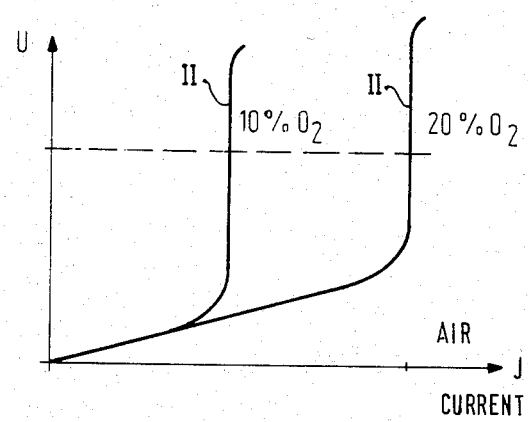
FIG. 1 is a graph of current (abscissa) versus output voltage (ordinate) for two different oxygen levels within the gas and illustrating output characteristics derived from the sensor.
Figure 2:
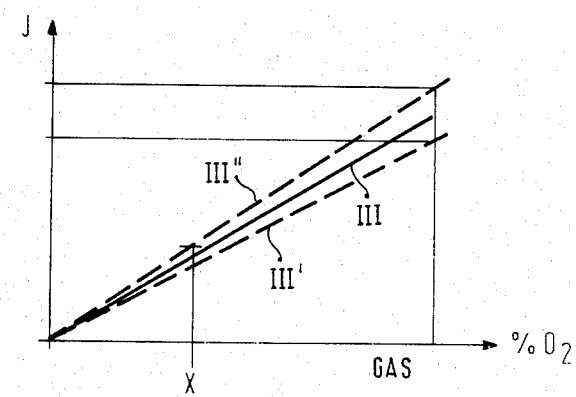
FIG. 2 is a graph of sensor current in dependence on oxygen of the test gas.

The sensor is an oxygen sensor which responds to partial pressure of oxygen in the exhaust gas from the internal combustion engine, or the heating installation, respectively. A test voltage is applied to the electrodes of the sensor. A measuring current will flow through the solid electrolyte of the sensor due to oxygen ion diffusion through the solid electrolyte body of the sensor. The level of the measuring current is limited by the diffusion speed of oxygen and depends on the concentration of oxygen in the gas to be sensed or tested. Changes in voltage of the test voltage source within a predetermined range do not affect the current flow, under stationary conditions, since the current flow will be determined solely by the diffusion speed. The characteristics of the sensor of this type are illustrated in FIG. 1, in which the graph I is drawn to represent oxygen partial pressure of 10% oxygen in the test gas, and the graph II of 20% oxygen. As can be seen, variations of voltage within a predetermined range do not affect the current flow of the sensor, the current, however, varying substantially with differences in oxygen concentration. The current which flows through the sensor, and which varies in dependence on oxygen concentration, is shown in FIG. 2 in the solid line graph III. The voltage range of operation of the sensor—see FIG. 1—within which the sensor is essentially unaffected, is in the order of about 0.5 V to 1.5 V for a sensor as described in the aforementioned referenced application U.S. Ser. No. 213,049, now U.S. Pat. No. 4,356,065.

Various changes occur in the operating characteristics of current-limiting sensors with time. Variations are due to changes in the sensor itself, or changes in the surrounding equipment, or conditions or apparatus to which the sensor is exposed. Drift of the sensor is frequently irreversible. Monitoring of the sensor is thus important so that accessory equipment can be recalibrated so that the control output derived from the sensor will become essentially independent of its environmental condition or time of its installation. It is difficult to recognize a shift in the working point of current-limiting sensors. For example, deposit of dirt on the sensor causes a shift in the operating characteristics; excessive heating also may cause a shift. Two shifted or changed operating characteristics, which may be irreversible, are shown in broken lines III', III'' in FIG. 2.

In accordance with the present invention, the sensor is calibrated by exposing it from time to time to ambient air, of known oxygen concentration. Since automotive vehicles, as well as many heating or furnace installations, are not operating continuously around the clock, use of ambient air is feasible and eminently suitable as a reference gas. Air, as well known, has an oxygen content of 20.8%. When the combustion process is interrupted, it is thus possible to calibrate the sensor. In many instances, for example upon contamination of the sensor, only the slope of the characteristic curve changes, as seen in FIG. 2. It has been determined, in accordance with a feature of the invention, that only the slope of the characteristic changes, as seen in FIG. 2, thus a single test value can be obtained and, based on the single measured value, the entire sensor characteristic can be matched to the new test value so that a single sensor value permits recalibration of the sensor or its accessory apparatus throughout its entire operating range.

Figure 3:
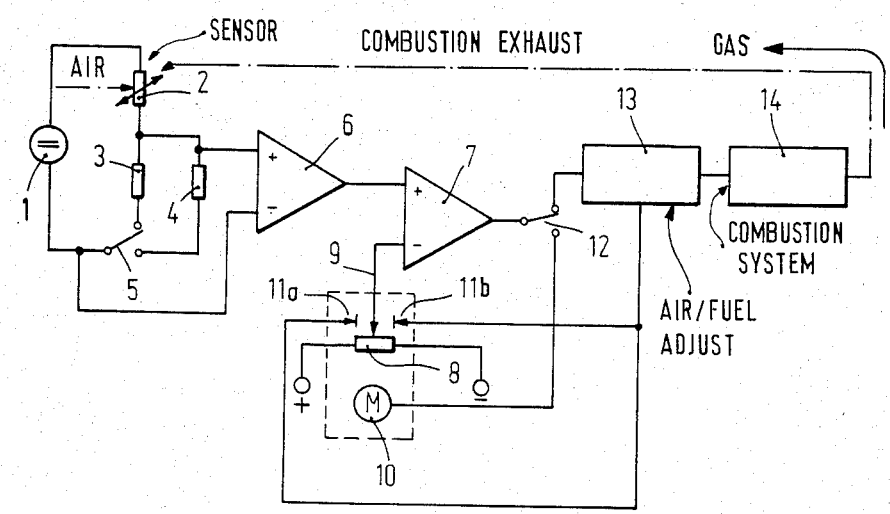
FIG. 3 is a schematic circuit diagram illustrating a first embodiment of the test and calibration system of the present invention.

FIG. 3 illustrates a system which permits control and recalibration. A dc source 1 is connected to a current-limiting sensor 2, shown as a variable resistor element since, in reflected terms, its resistance changes with change in oxygen concentration to which the sensor is exposed. A measuring resistor 3 is serially connected to the sensor in the circuit with the dc source 1 which, for example, may provide a regulated output voltage on the order of about 1 V. The circuit further includes a calibrating resistor 4 which can be connected to the source 1, selectively by a transfer switch 5. A differential amplifier, for example an operational amplifier 6, has its inverting input connected to one terminal, for example the negative terminal of the source 1. Its direct input is connected to the sensor 2. The output of the differential amplifier 6 is connected to the direct input of the differential amplifier 7 which, for example, may be an operational amplifier. The inverting input of differential amplifier 7 is connected to the tap point 9 of a potentiometer 8. The potentiometer 8 is connected to a dc source. The limits of travel of the slider on tap 9 of the potentiometer are determined by two end switches 11a, 11b. The switches 11a, 11b provide an output signal when the slider or tap 9 engages either one of the end or limit switches 11a, 11b. The switches 11a, 11b are connected to a controller 13. The slider or tap 9 is moved by a motor 10 which is connected through a transfer switch 12 to the output of the differential amplifier 7. The second terminal of the transfer switch 12 is connected to the controller 13 which, in turn, controls an air/fuel adjustment element in a combustion system 14. When the combustion system 14 is an IC engine, the air/fuel element 13 may, for example, be a fuel injection system, a carburetor or the like. The current-limiting sensor is exposed to the exhaust gases from the combustion system 14 and determines the oxygen concentration within the exhaust gases therefrom.

Operation: In operation of the combustion system 14, transfer switches 5 and 12 are connected as shown in the solid line positions in FIG. 3. The current flowing through the sensor 2 will cause a voltage drop across the measuring resistor 3, which is applied to the differential amplifier 6 which, in turn, provides an output signal to differential amplifier 7, the output of which is connected to the air/fuel adjustment element 13 to control the air/fuel composition of the combustion system 14.

Upon disconnection of the combustion system 14, for example upon stopping of an IC engine, ambient air is applied to the sensor 2, for example by blowing fresh ambient air against the sensor 2 from a blower (not shown). In many cases, however, it is sufficient to wait for some time until the duct, or manifold in which the sensor 2 in installed has ambient air applied thereto by ingress, for example through the muffler of an IC engine. When—based on experience, for example—the sensor 2 is exposed to ambient air, transfer switches 5, 12 are conjointly operated to change over to the position not shown in FIG. 3. This places the calibrating resistor 4 in circuit with the differential amplifier 6 and the motor 10 in circuit with the differential amplifier 7.

The calibrating resistor 4 is so dimensioned that it has the same voltage drop thereacross when the sensor 2 is exposed to ambient air as the voltage drop across measuring resistor 3 when the sensor 2 is subject to operating conditions. This voltage is amplified in the differential amplifier 6 and compared with a previously derived reference value which is connected to the inverting input of the differential amplifier 7. If the operating data of the current-limiting sensor 2 have not changed, the values will be the same for either switch position of switches 5 and 12, and no control or recalibration step will occur. If, however, a deviation is sensed, that is, if the value as measured by the differential amplifier 7 determines a deviation, that is, that the current of the sensor is too high, or too low, the conclusion can be reached that the sensor, under standard conditions, will operate with excessively high or excessively low current. The motor 10, then, is commanded by the output from the differential amplifier 7 to null this deviation by changing the tap or slider 9 of the potentiometer until the system is again in balance. This change simply changes the slope of the operating characteristics—see FIG. 2.

A higher or lower voltage on slider 9 thus automatically compensates for deviations in operation of the sensor 2. The test point x (FIG. 2) will, at a suitable corresponding oxygen concentration, then have the same current thereon. If the deviation of the current flow of the sensor from original data is excessive, the tap or slider 9 will reach one or the other of the end stops or limits 11a, 11b. Upon reaching the end or limit switches, the air/fuel adjustment element is disabled and a fixed value, for example introduced therein as a fixed dc control value or the like is applied as a reference to the combustion system 14, while, simultaneously, an alarm can be provided.

Various switches corresponding to the switches 11a, 11b can be placed along the travel or path of the slider or tap 9. In many installations it is desirable to provide for early warning by placing two limit switches at the end portions of the potentiometer 8. When the first limit switch is reached, a preliminary warning indication is given, providing an output that the sensor is about to reach the end of its operating range; the air/fuel adjustment element is actually disabled, however, only when the second or final switch is reached.

The system of FIG. 3 is particularly simple and can be readily expanded or matched to many applications. It is eminently suitable for calibrating the current-limiting sensor. Calibration will be carried out only when the sensor is exposed to ambient air, which can readily be determined by suitable apparatus, for example by a timer.

Rather than applying ambient air to the sensor, by lapse of time or by blower, the sensor can be located in a bypass, or an air-bypass can be installed in the region of the placement of the sensor.

Any reference gas of known composition can be used; air is eminently suitable, but other definitely known mixtures of gases can be used.

Upon termination of the calibration step, the system is again changed over to the measuring position, that is, switches 5 and 12 are changed to the position in solid lines in FIG. 3. A timer can be used to effect or control change-over, the timer leaving the system in the calibrating mode for the time normally required for the motor to move the slider, for example from one maximum position to the other.

Figure 4:
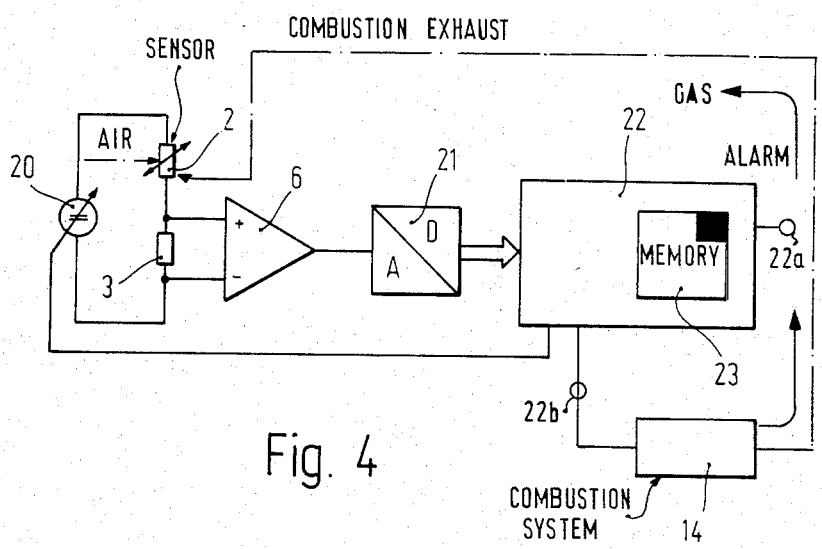
FIG. 4 is a schematic diagram illustrating another embodiment and using a micro computer.

The sensor calibration system can be simplified and further automated by using digital controls. A suitable embodiment is shown in FIG. 4.

A voltage source 20 of variable voltage value is connected to the current-limiting sensor 2. The measuring resistor 3 is serially connected with the variable voltage sensor 2. The differential amplifier 6 is connected across the measuring resistor 3 as in the embodiment of FIG. 1. The differential amplifier 6 senses the voltage dropping across the measuring resistor 3 and applies this voltage to an analog/digital converter 21, which is connected via a data bus to a micro computer 22, which thus receives the measured voltage in form of a digital signal. Micro computer 22 includes a memory section 23. The micro computer 22 has an output which is connected to the combustion system 14, and a further control output connected to the dc source 20.

Operation: Generally, the sequence of testing the combustion exhaust gas derived from the combustion system 14 and, at a different time, to derive an output based on ambient air, is shown in form of a chain-dotted arrow applied to sensor 2, is the same as that of FIG. 3. The primary difference is that the sequencing of the steps is computer controlled. The sensor signal is transferred into a digital signal by the analog/digital (a/d) converter 21, to there be compared with a reference value stored in the memory 23. The combustion system 14 is suitably controlled by the microcomputer 22. The micro computer additionally can control a timing network to control switch-over to calibration operation in which, after air has been introduced to the sensor as schematically indicated by the chain-dotted arrow, the current is then measured and recorded in an addressed memory location. In a simple case, a new measured value is then introduced into the memory location in which, previously, the desired or reference value had been stored. This is done, of course, only if the newly measured value is within tolerance limits. Before recording, the measured value therefore is compared with limiting values. If the first limiting value is obtained, an alarm output is derived from terminal 22a; if a second and higher limiting value is reached, the combustion system 14 is no longer controlled from the output of the micro computer 22 under control of the measured value and, rather, the output terminal 22b of the computer 22 is switched over within the computer to an emergency program stored in memory 23.

The system utilizing a micro computer permits adaptation to determine a trend. The memory 23 is arranged to store a first reference value and then, upon a subsequent measurement, store the next measured value which will form a value for a subsequent measurement. If the respective steps are equidistant, a trend can be determined by extrapolation so that the next two or three calibrating intervals can be determined from the first two. Simple extrapolation based on the two last reference values can be used. A more accurate mode of matching can be obtained by using a parabolic matching to the last three values, and forming a derivation from the last reference value and extrapolation by calculation of a balance curve which, generally, exponentially tends to reach an asymptotic line.

Various ways to sense a trend can be used, among them the three ways referred to. The various ways can be used in combination with each other, or in steps, particularly if the number of measured values is insufficient for complete calculation. Various types of micro computers are available commercially to carry out such computation steps.

Figure 6:
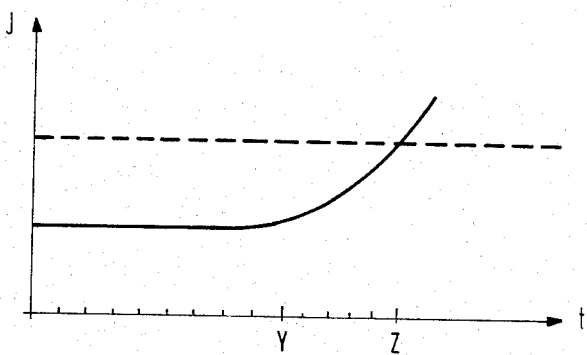
FIG. 6 is a graph of sensor current (ordinate) with respect to time.

FIG. 6 illustrates the basis for following a trend. By following a trend it is possible to determine early if a critical value is reached and to provide a preliminary alarm, or indication to the operator to exchange the sensor for a new one without requiring interference at that time with the combustion system 14, since the sensor is still operative. The operator, thus, has time for one to two calibrating intervals before the combustion system 14 would be disabled or the sensor would have reached the operating limit, and early exchange of the sensing element can thus be indicated. The old sensor, at that time, will not yet have exceeded its maximum operating limit, yet a sensor which is still good need not be exchanged merely because a predetermined operating time has elapsed.

FIG. 6 illustrates change in limit current with respect to time. At time Y, the current begins to change. At time Z, the sensor has reached a limit beyond which it does not operate satisfactorily. By determining the slope of the curve between succeeding intervals, the time Y can be determined, or any intermediate time between Y and Z. If the calibrating intervals are uniform, the time between intervals need not be considered. If the calibrating intervals are not uniform, however, the micro computer must be capable of also sensing time intervals.

The calibrating arrangement of FIG. 4 also permits compensation for drift due to time, aging, or other influences, and which also changes the characteristic curve not only in its slope, but also in its aspect. Some sensors have characteristics which do not exhibit linear changes, that is, in which the characteristics are essentially straight lines but rather which have characteristics in which current-voltage relationships are non-linear, that is, are along a curved path. Such a curved path is shown, for example, in FIG. 5. If the characteristic of the curved path and the change of the characteristic of the sensor, or the type of sensor is known, then it is possible to utilize the memory 23 in a micro processor to store the functional relationship. Of course, it would equally be possible to construct a potentiometer 8 (FIG.

Figure 5:
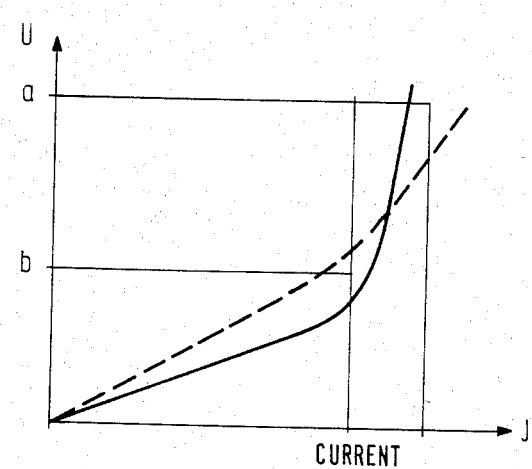
FIG. 5 is a detailed view of a portion of a sensor characteristic of the graph of FIG. 1.

3) which has a non-linear resistance characteristic upon movement of the slider or tap 9 thereover; matching of such resistance characteristics to individual sensors is difficult and expensive, however, and frequently not feasible. Matching of storage of a function in a memory with an actual sensor, or type of sensor is much easier, and it is readily possible to store in the memory 23 a family of characteristic curves and then to address that one of the characteristic curves of the family according to which the control or calibration characteristic is to be carried out. The arrangement of FIG. 4 further permits to test a current-limiting sensor as such. Some sensors exhibit changes which detract from the current-limiting operating thereof and make the sensor sensitive with respect to other parameters than merely oxygen content, for example, temperature of the sensor. A typical characteristic is illustrated in FIG. 5. The solid line of FIG. 5 shows, in a highly exaggerated and enlarged scale, the characteristic of a perfectly operating sensor. The broken line, however, illustrates the characteristic of a current-limiting sensor which has been damaged, or operates improperly.

Checking of the Sensor: The voltage of the dc source 20, FIG. 4 is changed in steps and the limit current is sensed or tested. The limit current as actually sensed or tested is compared with the stored or ideal limit current and changes can be noted to thereby recognize malfunction of the sensor. Such interrogation of sensor operation, for example, in steps, can readily be carried out by a micro processor or micro computer. The slope of the curve, which is derived from the difference in current with respect to difference in voltage can also be used to determine if the sensor has been damaged if the change in slope differs from that which is stored, or should ideally occur. FIG. 5 illustrates, as an example, a two-point check, in which the sensor current is determined at the voltages a and b. If the current of the sensor, with the two voltage values, is within a certain tolerance range, then the sensor is in order; if the resulting slope is beyond the tolerance range, at either side thereof, the sensor is defective.

In accordance with the feature of the invention, the dc voltage of the source 20 may have a variation or undulation superimposed thereon, which, for example, is periodically varying and may be in form of a triangle, wave, sawtooth wave, or sine wave, or some other periodically changing function. The limit current then also must fall within a predetermined tolerance ranges or limits. To reduce dynamic effects, the frequency of such superposed wave should be held small, since, otherwise, the limit interval or tolerance range must be extended. A suitable frequency range is in the order of about 1 Hz.

The measuring processes here described are not limited to current-limiting sensors in furnaces, heating installations or combustion engines in motor vehicle, or for stationary installations; they can be used in all installations in which current-limiting sensors are employed and where a gas with a known, or constant oxygen content can be applied to the sensing point so that the sensor will be exposed thereto. Correction in the control loop, by changing the parameters thereof, always permits then operation of an actual control loop at optimum parameter adjustment. The method and apparatus further permit the use of current-limiting sensors which have characteristics, or operating curve characteristics which vary from a standard or from design values without interfering with control loop behavior by matching the parameters of the control loop which includes the sensor to the sensor voltage/current transfer characteristics under varying oxygen conditions.

Various changes and modifications may be made and features described in connection with any one of the embodiments may be used with the other within the scope of the inventive concept. It can be assumed that the sensor in an automotive vehicle is exposed to ambient air when the temperature surrounding the sensor has reached the same as ambient temperature; thus, if equality between, for example, engine temperature and ambient temperature is established, it can be assumed that ambient air surrounds a sensor installed in an automotive vehicle and that a test for calibration purposes can then be carried out.

We claim:

1. Method of monitoring the operation and calibration of a current-limiting type gas sensor (2) adapted for exposure to a combustion exhaust gas from a combustion system (14), which gas is to be tested for presence of a predetermined component thereof, and having an output connection to an evaluation circuit to translate the magnitude of the limit-current produced by said sensor into an output signal representative of the concentration of said predetermined component in the gas,
 comprising the steps of
 intermittently subjecting the sensor (2) to ambient air, by waiting a predetermined period of time after the last operation of said combustion system, sufficient to permit ambient air to penetrate the system and purge said system of residual combustion gases, then measuring the then-obtaining output of the sensor;
 providing a standard reference value representative of sensor output when subjected to said ambient air;
 comparing the measured limit-current output from the sensor, while subjected to ambient air, with such standard reference value;
 obtaining a deviation signal if the measured limit-current output and the standard reference value do not agree;
 determining whether the magnitude of said deviation signal exceeds a present value and, if not, storing said measured limit-current output as an updated one of a plurality of sensor operating point reference values;
 deriving from said plurality of stored operating point values a standard sensor operating characteristic curve or function; and
 extrapolating the sensor characteristic curve or function beyond the values from which said curve or function was derived.

2. Method according to claim 1, further including the step of
 deriving an alarm signal if the preset value is exceeded.

3. Method according to claim 2, further including the step of utilizing the output from the sensor in a control apparatus (13, 14);
 and interrupting application of the sensor ouput to the control apparatus if the deviation signal exceeds the preset value.

4. Method according to claim 1, further including the step of
 updating the magnitude of the standard reference value to conform to said measured output only if the deviation signal is greater than zero and below a preset value.

5. Method according to claim 1, further including the step of providing an operating voltage to said sensor;

and further including the step of varying the voltage applied to the sensor about a standard, or average value when the sensor is exposed to the ambient air, and the measuring step includes measuring the sensor current as the voltage is being varied.

6. Method according to claim 5, wherein said variation is carried out at a repetition rate having a frequency of up to about 1 Hz.

7. Method according to claim 1, wherein the sensor is used in combination with a combustion system (14);

and wherein said step of subjecting the sensor to ambient air is carried out shortly before placing the combustion system in a combustion mode of operation.

8. Method according to claim 1, further including the steps of providing a critical or maximum sensor output reference value, indicative of sensor failure, determining whether said sensor output exceeds said maximum value, and executing said step of storing said measured limit-current output only if said maximum value is not exceeded.

9. The method of claim 8, further including the step of deriving an alarm signal if said maximum value is exceeded.

10. The method of claim 8, further including the steps of utilizing the output from the sensor in a control apparatus, and interrupting application of the sensor output to the control apparatus if said maximum value is exceeded.

11. The method of claim 1, further including the steps of providing a maximum sensor output reference value, indicative of sensor failure, determining whether said extrapolated curve reaches said maximum value within a predetermined time period, and, if so, deriving a preliminary alarm signal.

* * * * *